(12) United States Patent
Rabizadeh et al.

(10) Patent No.: US 10,525,040 B2
(45) Date of Patent: Jan. 7, 2020

(54) COMPOSITIONS AND METHODS OF RIT1 INHIBITION

(71) Applicants: NANTBIO, INC., Culver City, CA (US); NANTOMICS, LLC, Culver City, CA (US); NANT HOLDINGS IP, LLC, Culver City, CA (US)

(72) Inventors: Shahrooz Rabizadeh, Culver City, CA (US); Oleksandr Buzko, Los Angeles, CA (US); Paul Weingarten, Anaheim, CA (US); Heather McFarlane, Los Angeles, CA (US); Connie Tsai, Culver City, CA (US); Stephen Charles Benz, Santa Cruz, CA (US); Kayvan Niazi, Culver City, CA (US); Patrick Soon-Shiong, Culver City, CA (US)

(73) Assignees: NantBio, Inc., Culver City, CA (US); NantOmics, LLC, Culver City, CA (US); Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 15/738,353

(22) PCT Filed: Jun. 29, 2016

(86) PCT No.: PCT/US2016/040212
§ 371 (c)(1),
(2) Date: Dec. 20, 2017

(87) PCT Pub. No.: WO2017/004274
PCT Pub. Date: Jan. 5, 2017

(65) Prior Publication Data
US 2018/0185335 A1  Jul. 5, 2018

Related U.S. Application Data

(60) Provisional application No. 62/186,316, filed on Jun. 29, 2015.

(51) Int. Cl.
| | | |
|---|---|---|
| *A61K 31/4196* | (2006.01) | |
| *A61K 45/06* | (2006.01) | |
| *A61K 31/538* | (2006.01) | |
| *A61P 35/00* | (2006.01) | |
| *A61K 31/4155* | (2006.01) | |
| *A61K 31/4178* | (2006.01) | |
| *A61K 31/4439* | (2006.01) | |

(52) U.S. Cl.
CPC ...... *A61K 31/4196* (2013.01); *A61K 31/4155* (2013.01); *A61K 31/4178* (2013.01); *A61K 31/4439* (2013.01); *A61K 31/538* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 2014/0228367 A1 | 8/2014 | Flynn |
| 2014/0235702 A1 | 8/2014 | Nikolovska-Coleska et al. |

FOREIGN PATENT DOCUMENTS

| | | |
|---|---|---|
| WO | 98-16227 A1 | 4/1998 |
| WO | 02-24682 A1 | 3/2002 |

OTHER PUBLICATIONS

Anderson (Chem and Biol 10:787-797, 2003) (Year: 2003).*
Thiel (Nature Biotechnol 2:513-519, 2004) (Year: 2004).*
El-Kerdaway et al (Arch Pharm Res 13:142-146, 1990) (Year: 1990).*
Lyne, P. D. et al., "Identification of amidoheteroaryls as potent inhibitors of mutant (V600E) B-Raf kinase with in vivo activity", Bioorganic & Medicinal Chemistry Letters, 2009 [Epub. Oct. 15, 2008], vol. 19, No. 3, pp. 1026-1029.
PCT Notification of Transmittal of the International Search Report and Written Opinion, PCT International Search Report and PCT Written Opinion issued for the corresponding PCT application No. PCT/US2016/040212, dated Jan. 16, 2017 (16 pages).

* cited by examiner

*Primary Examiner* — Craig D Ricci
(74) *Attorney, Agent, or Firm* — Lucas & Mercanti, LLP

(57) ABSTRACT

Various compounds, compositions, and methods for inhibition of Rit1 are presented. In especially preferred aspects, contemplated compounds and compositions are suitable for treatment of cancers and other diseases associated with Rit1 signaling.

5 Claims, 13 Drawing Sheets

A1233

| | H2110 | | BxPC3 | | H358 | | H460 | |
|---|---|---|---|---|---|---|---|---|
| | pAkt_30min | pERK_30min | pAkt_30min | pERK_30min | pAkt_30min | pERK_30min | pAkt_30min | pERK_30min |
| 1233 | XXXXXX | X | X | | | | | |
| 1184 | XXXXX | XX | | | | | X | |
| 1212 | XXXX | XXXX | X | X | | | X | |
| 1238 | XX | | | | | | XX | |
| 1181 | X | | | | | | | |
| 1194 | X | | XX | | | | | |
| 1205 | X | | X | | | | | |
| 1197 | X | XX | | | | | | |
| 1229 | X | | | | | | | |

| | Panc1 | | H2122 | | HCT116 | MiaPaca2 |
|---|---|---|---|---|---|---|
| | pAkt_30min | pERK_30min | pAkt_30min | pERK_30min | pAkt_30min | pAkt_30min |
| | X | | X | X | | |
| | | | X | X | X | X |
| | | | X | | | |
| | | | X | | | |
| | | | X | | | |
| | | X | X | X | | |
| | | | X | | | |

FIG. 6B

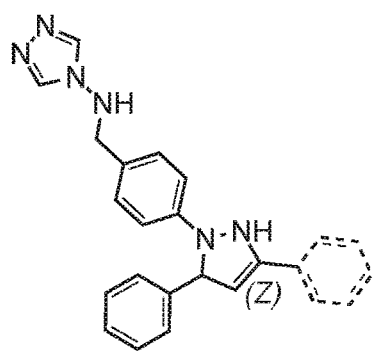
A1233
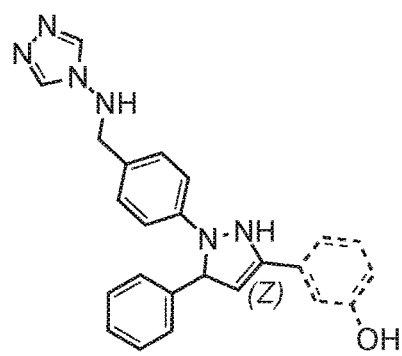
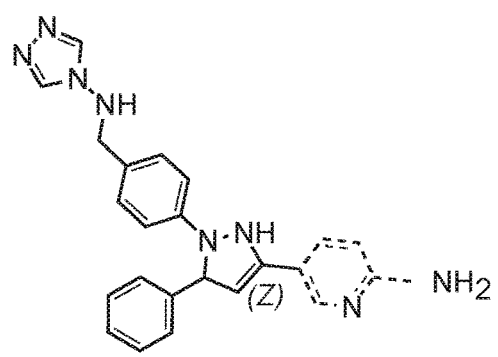
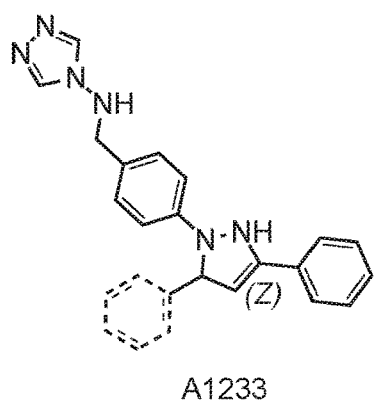
A1233
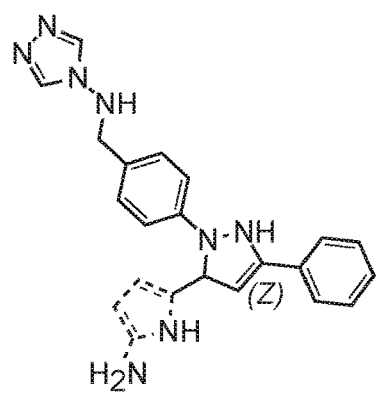
*FIG. 8A-1*
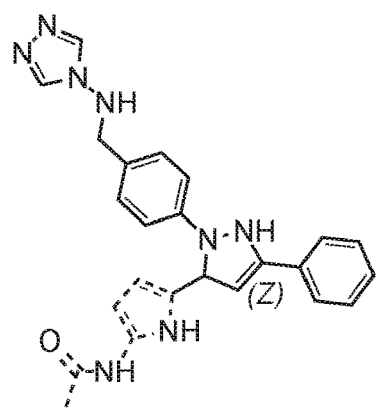

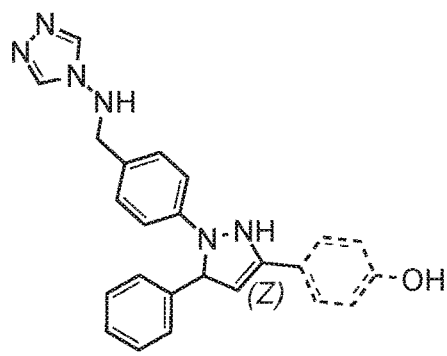
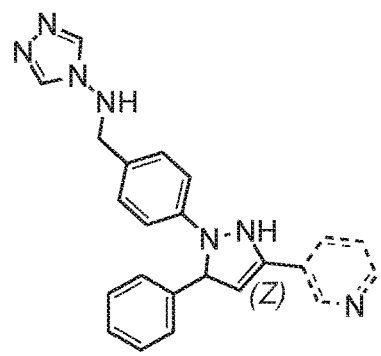
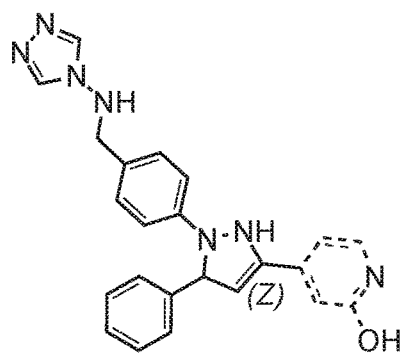
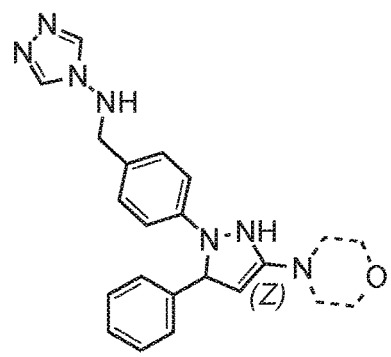
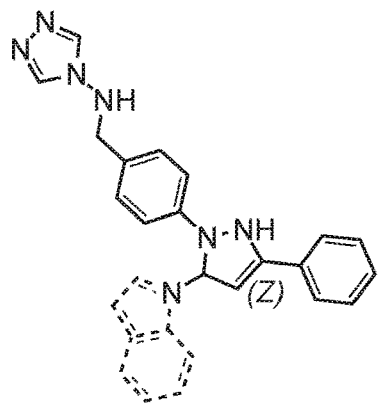
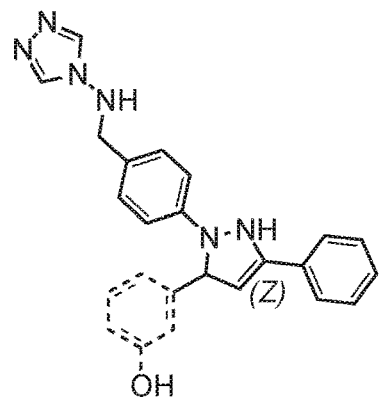
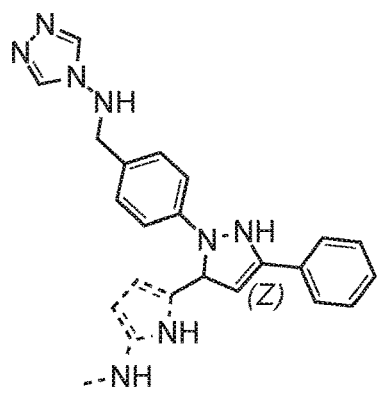
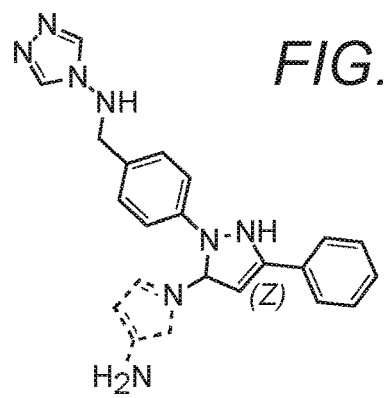
FIG. 8A-2

COMPOSITIONS AND METHODS OF RIT1 INHIBITION

CROSS-REFERENCE TO RELATED APPLICATIONS

This application is a 371 of PCT/US2016/040212, filed Jun. 29, 2016, which claims the benefit of U.S. Provisional Patent Application Ser. No. 62/186,316, filed Jun. 29, 2015.

FIELD OF THE INVENTION

The field of the invention is compounds, compositions, and methods of inhibiting Rit1, especially as it relates to treatment of cancers.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Rit1 is a member in the subfamily of Ras-related GTPases as can be seen from the alignment of related Ras-type sequences shown in Prior Art FIG. 1A. Rit1 is involved in regulating p38 MAPK-dependent signaling cascades related to cellular stress, and is thought to cooperate with nerve growth factor to promote neuronal development and regeneration. Here, Rit1 seems to play a crucial role in coupling nerve growth factor (NGF) stimulation to the activation of both EPHB2 and MAPK14 signaling pathways and in NGF-dependent neuronal differentiation. Rit1 further seems involved in ELK1 trans-activation through the Ras-MAPK signaling cascade that mediates a wide variety of cellular functions, including cell proliferation, survival, and differentiation. Prior Art FIGS. 1B and 1C schematically illustrate involvement of Rit1 in various signaling pathways.

Rit1 is also known to be associated with certain diseases (e.g., Noonan syndrome) and certain cancers (e.g., lung cancer, colorectal cancer, thyroid cancer) and pheochromocytoma. More recently, somatic mutations in RIT1 were reported in a small proportion of lung cancer that clustered in a hotspot near the switch II domain of the protein (*Oncogene* 2014; 33, 4418-4423). Rit1 was also reported as a potential driver oncogene (*Mol Cancer Ther* 2013 12; C140), but no indication of any inhibitor was provided. In further reports, elevated expression of RITZ was shown to correlate with poor prognosis in endometrial cancer (*Int J Clin Exp Pathol* 2015; 8(9):10315-10324).

However, despite the at least tentative association with some malignancies and other diseases, no specific and effective Rit1 inhibitor has been reported to date. Therefore, there remains a need for compounds, compositions, and methods of inhibiting Rit1, particularly for the purpose of treating Rit1 associated diseases and cancer.

SUMMARY OF THE INVENTION

The inventive subject matter is directed to compounds, compositions, and methods of inhibiting Rit1, and especially inhibiting Rit1 in vivo as therapeutic modality to treat cancers associated with Rit1 amplification, overexpression, and/or over-activity. Especially preferred compounds are small molecule compounds with multiple aromatic rings that interact with a binding fold on the Rit1 protein proximal to the GTP binding motif.

In one aspect of the inventive subject matter, a pharmaceutical composition is contemplated that comprises a compound having a structure according to Formula I and a pharmaceutically acceptable carrier

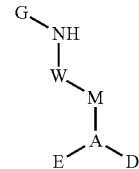

Formula I in which wherein G is an optionally substituted 5- or 6-membered ring, W is $(CH_2)_n$, S(O), $SO_2$, or null, and n is an integer between 1-3, M is an optionally substituted 6-membered ring, A is a 5-membered ring, and E and D are independently an optionally substituted 5- or 6-membered ring, wherein the compound is present in the pharmaceutical composition in an amount effective to inhibit Rit1 when administered to a patient in need thereof.

In further contemplated aspects, G is a heterocyclic or aromatic ring, and especially contemplated rings include pyrrole, pyrrolidine, thiophene, thiolane, pyrazole, imidazole, pyrazolidine, imidazolidine, thiazole, isothiazole, thiazolidine, isothiazolidine, triazole, thiadiazole, oxadiazole, tetrazole, pyridine, piperidine, diazine, piperazine, oxazine, morpholine, thiazine, trizine, and tetrazine. It is also contemplated that G is substituted with at least one radical selected form the group consisting of $NH_2$, $NO_2$, OH, O, S, SH, lower alkyl, and halogen. In still further preferred aspects, W is $CH_2$ and/or M is a heterocyclic ring (e.g., piperidine, or cyclohexadiene) or a phenyl, which may be substituted with at least one radical selected form the group consisting of $NH_2$, $NO_2$, OH, O, S, SH, lower alkyl, and halogen. Similarly, A may be an aromatic ring, or pyrazolidine or pyrazoline. In still further contemplated aspects, at least one of E and D may be an optionally substituted aromatic 6-membered ring or comprise a heteroatom or may have a fused ring coupled thereto. For example, E and/or D may be an optionally substituted phenyl, pyrrolidine, pyrrole, pyridine, or morpholine. Suitable substituents for E and D include $NH_2$, NHalkyl, NHacetyl, $NO_2$, OH, O, S, SH, lower alkyl, and halogen.

In an especially preferred aspect, the compound in contemplated pharmaceutical compositions may have a structure according to Formula Ia

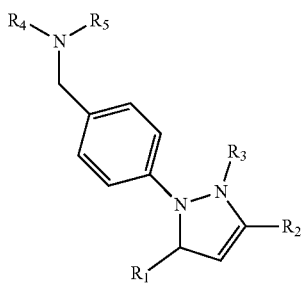

Formula Ia in which $R_1$, $R_2$, and $R_4$ are independently aryl, heteroaryl, heterocycle, or fused heterocycle, each optionally substituted, and in which $R_3$ and $R_5$ are independently hydrogen or lower alkyl. For example, $R_3$ and $R_5$ may be hydrogen, and/or at least one of $R_1$ and $R_2$ may be a phenyl group. $R_4$ may be a 5- or 6-membered heterocyclic ring (e.g., a triazole, an imidazole, or a pyridine).

In another aspect of the inventive subject matter, a pharmaceutical composition is contemplated that comprises a compound having a structure according to Formula II and a pharmaceutically acceptable carrier

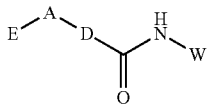

Formula II in which E is an optionally substituted fused ring system having two rings, A is $CR_1R_2$, S(O), or $SO_2$, wherein $R_1$ and $R_2$ are independently selected form the group consisting of H, halogen, and lower alkyl, in which D and W are independently an optionally substituted 6-membered ring, and in which the compound is present in the pharmaceutical composition in an amount effective to inhibit Rit1 when administered to a patient in need thereof.

In further contemplated aspects, E may comprise a phenyl, a heterocyclic ring, or a phenyl ring fused to a morpholino ring. It should also be appreciated that E can be substituted with a radical selected form the group consisting of $NH_2$, $NO_2$, OH, O, S, SH, lower alkyl, and halogen. A is preferably $SO_2$ or $CH_2$, and/or D is cyclohexane or piperidine, while W may be an aromatic ring (e.g., phenyl or pyridine).

For example, contemplated compounds may have a structure according to Formula IIa

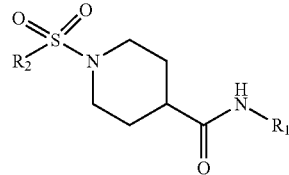

Formula IIa in which $R_1$ and $R_2$ are independently aryl, heteroaryl, heterocycle, or aryl fused to a heterocycle, wherein each of $R_1$ and $R_2$ are independently optionally substituted. For example, $R_2$ may comprise a phenyl or a heterocyclic ring, or a phenyl ring fused to a morpholino ring, while $R_1$ may comprise a phenyl or a pyridine.

Therefore, contemplated compounds may also have a structure according to Formula IIb

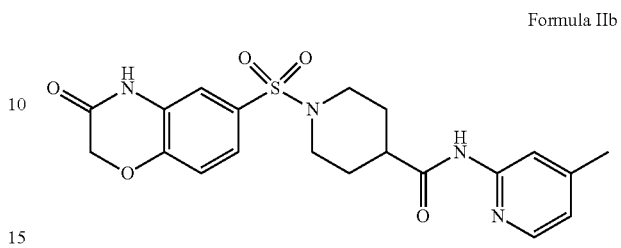

Formula IIb

Consequently, in yet another aspect of the inventive subject matter, the inventors also contemplate a method of inhibiting Rit1 in a mammal in which contemplated compounds and pharmaceutical compositions comprising such compounds are administered to the mammal, which may be diagnosed with a cancer. Most typically, the pharmaceutical composition is administered to the mammal under a protocol effective to reduce or even prevent cancer growth in the mammal. Viewed from a different perspective, the compounds and compositions presented herein are contemplated in the use and treatment of cancer or in the manufacture of a medicament for treatment of cancer or inhibition of Rit1 in a mammal o mammalian cell. Thus, the inventors also contemplate a method of treating cancer in a mammal (e.g., human) in which pharmaceutical compositions presented herein are administered to the mammal under a protocol effective to treat the cancer in the mammal. Such treatment may be accompanied by administration of a second drug Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

Prior Art

FIGS. 2A-2D are schematic illustrations of amplification/overexpression of selected genes associated with chromatin remodeling, and especially Rit1, in certain cancers.

FIGS. 6A-6B are graphs illustrating experiments demonstrating pAKT/pERK inhibition in cells (6A: BEZ235 is PI3K inhibitor, MEK Inhib II is MEK Inhibitor II; 6B: inhibition of pAKT and pERK using contemplated compounds).

FIGS. 8A-8B depict exemplary structures for Rit1 inhibitors contemplated herein.

DETAILED DESCRIPTION

Figure 1A:
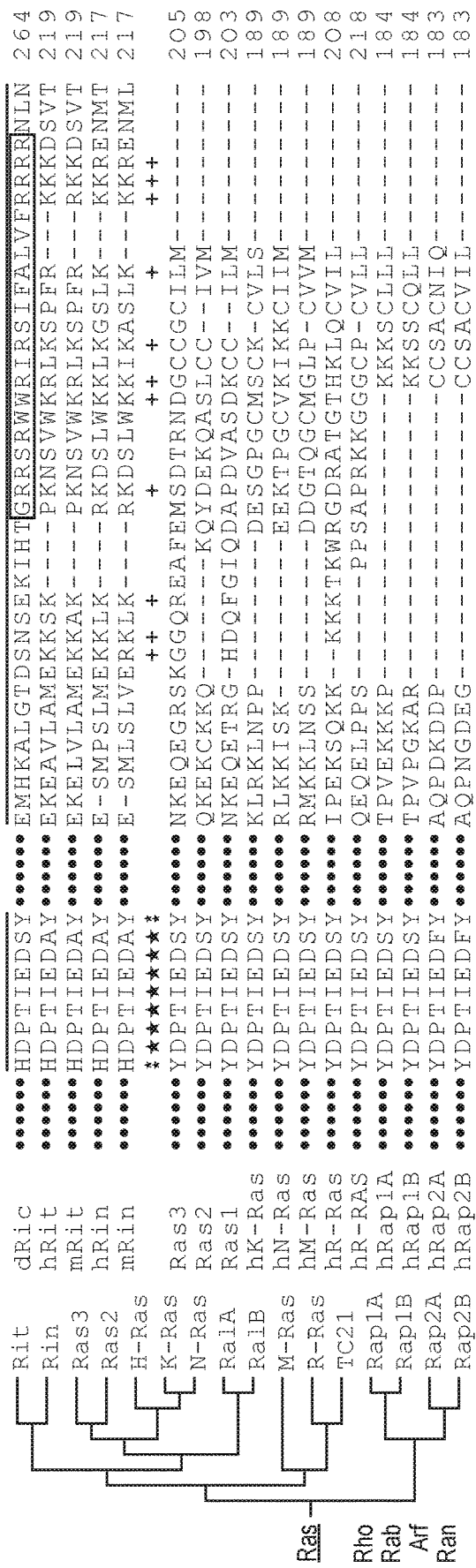
FIGS. 1A-1C are exemplary signaling pathways using Rit1 signaling.
Figure 1B:
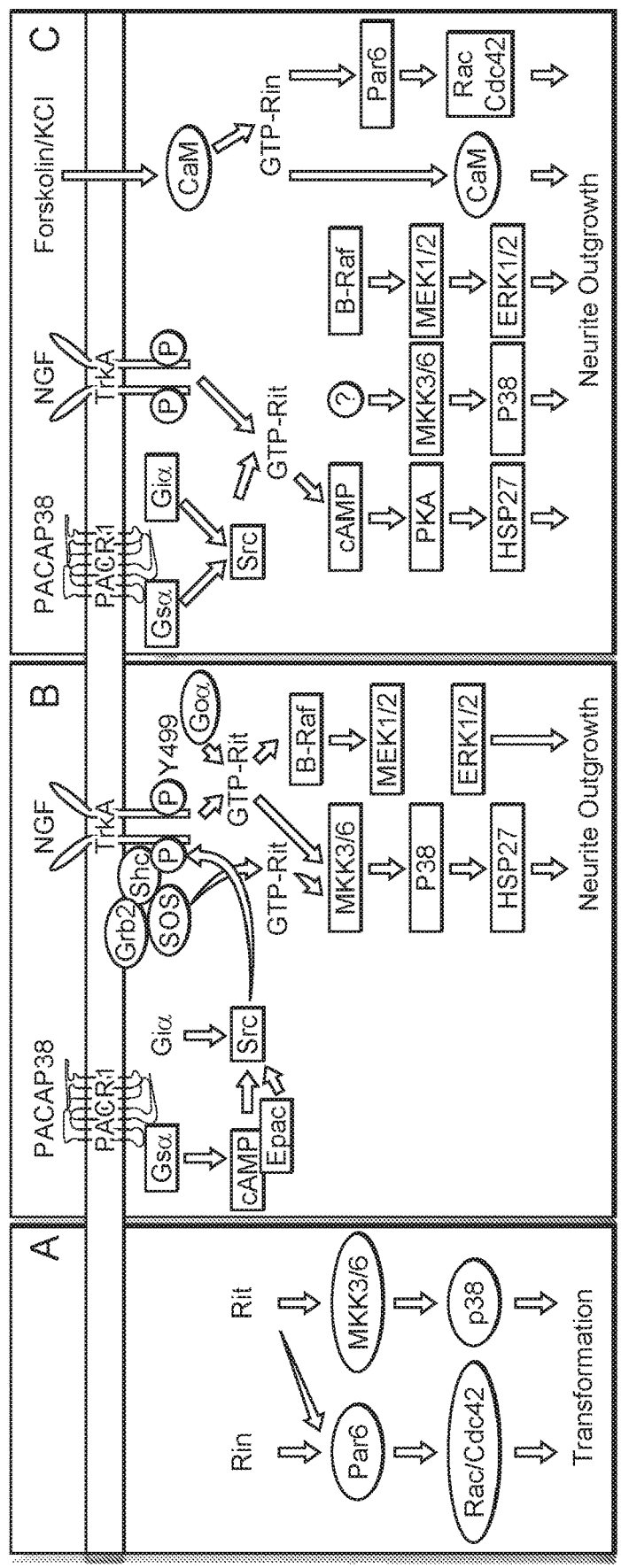
Figure 1C:
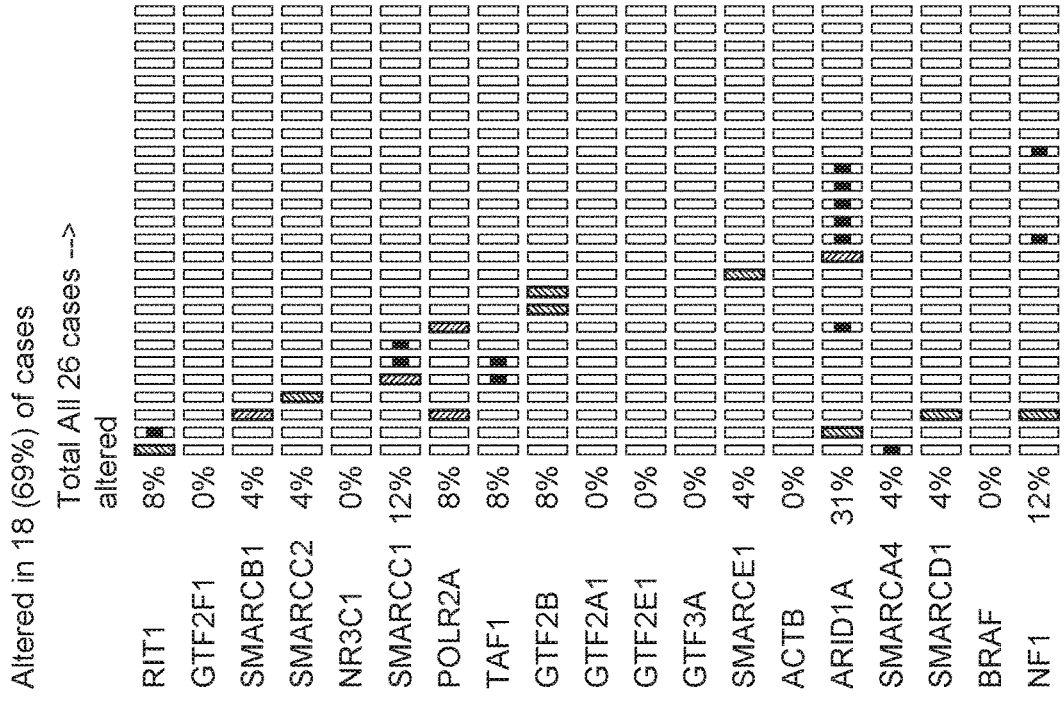
Figure 1C:
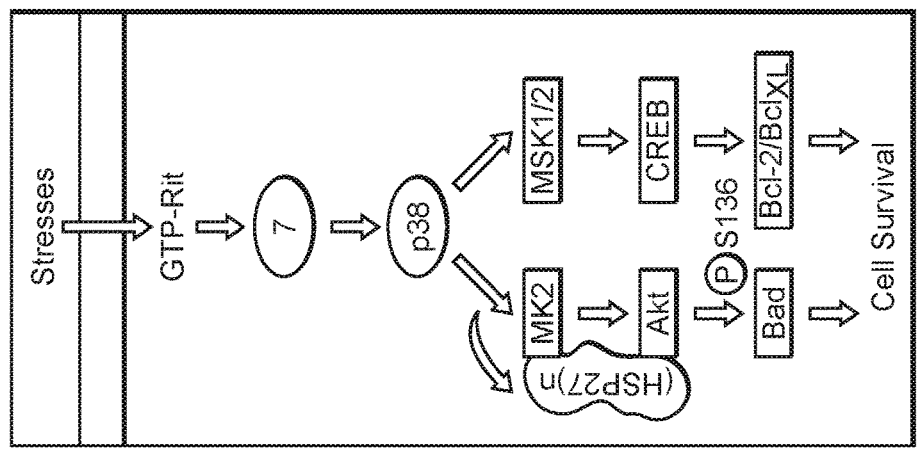
Figure 2B:
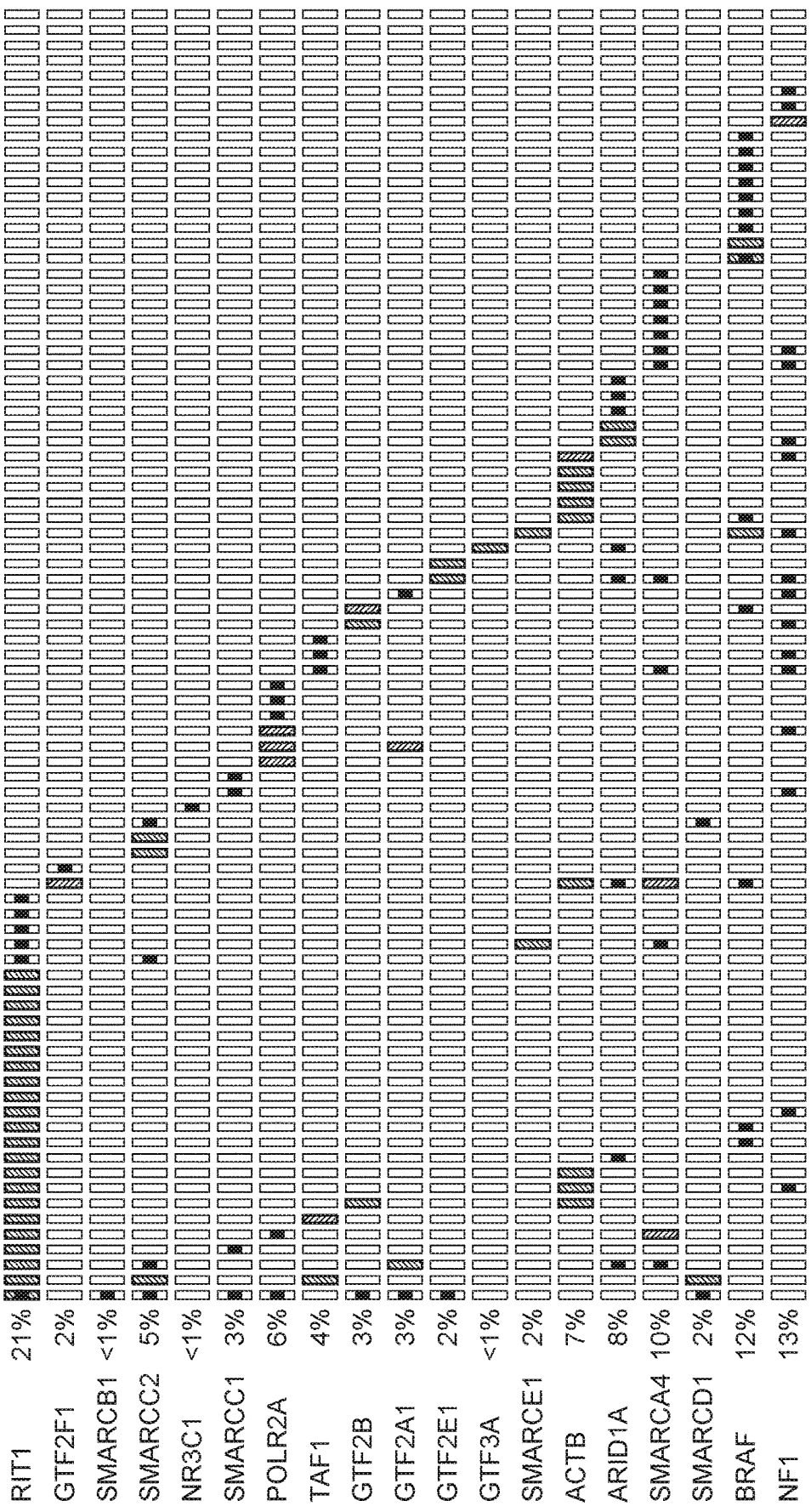
Figure 2C:
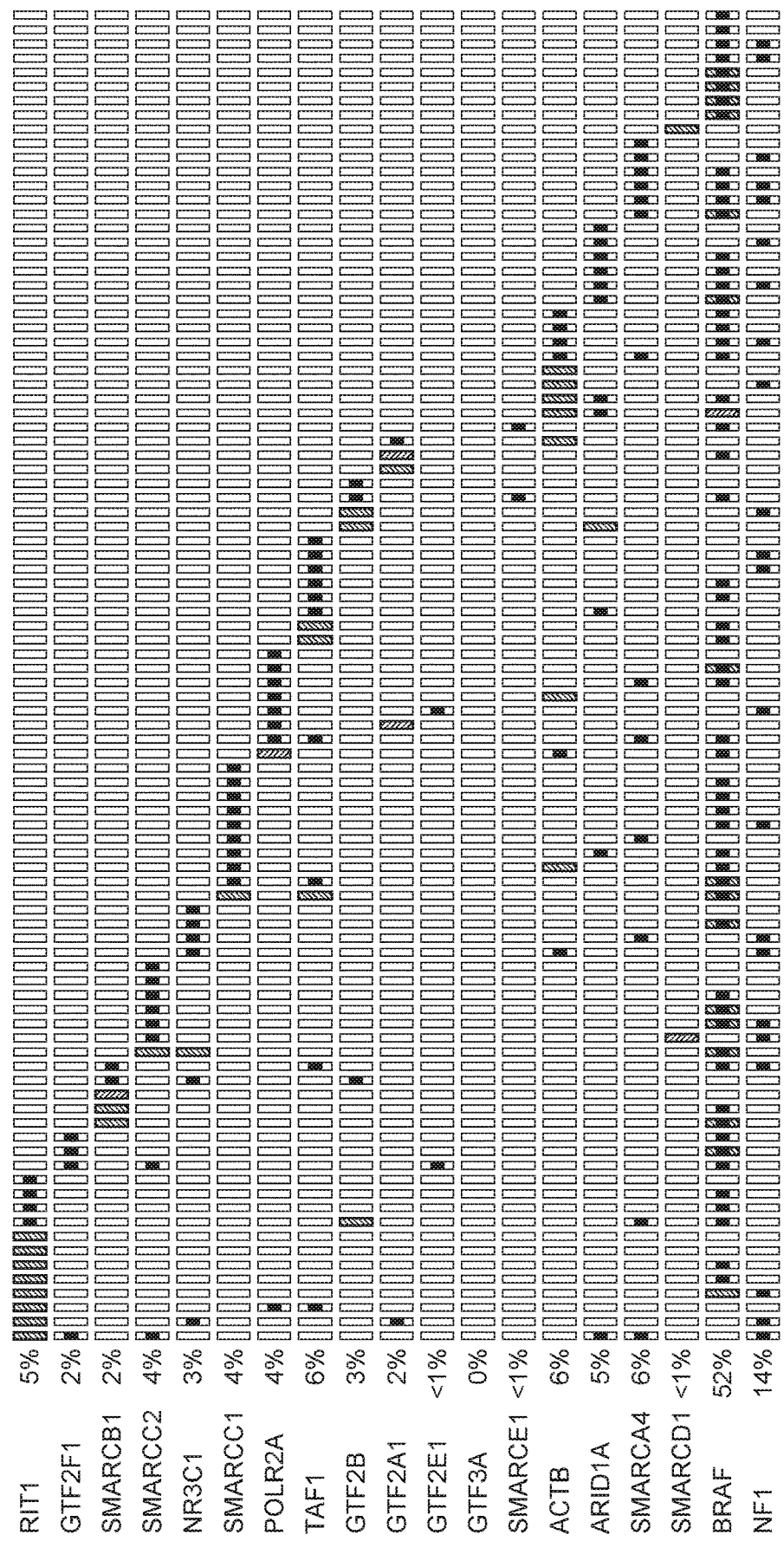
Figure 2D:
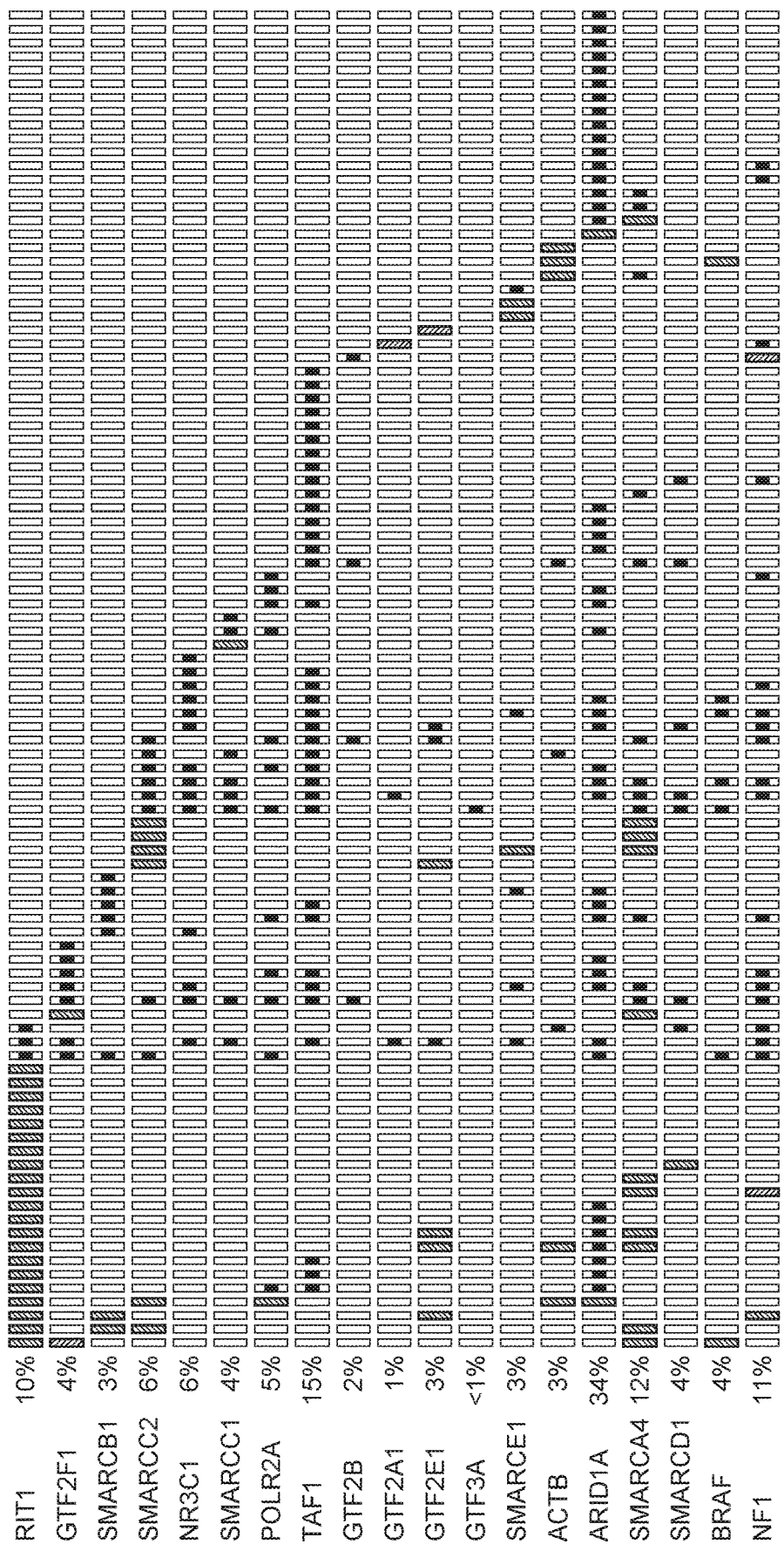

The inventors recently discovered that pAkt/pERK signaling in lung adenocarcinoma H2110 cells (M901) was driven by an oncogenic Rit1 mutant. The inventors also observed that functional alteration and especially amplification/overexpression of Rit1 and other chromatin remodeling associated genes was associated with certain cancers as is exemplarily shown in FIGS. 2A to 2D. Here, various proteins associated with chromatin remodeling by HSWI/SNF ATP-dependent complexes are shown for four different cancers (FIG. 2A: bladder cancer; FIG. 2B: lung adeno carcinoma; FIG. 2C: melanoma; FIG. 2D: uterine cancer).

Figure 3:
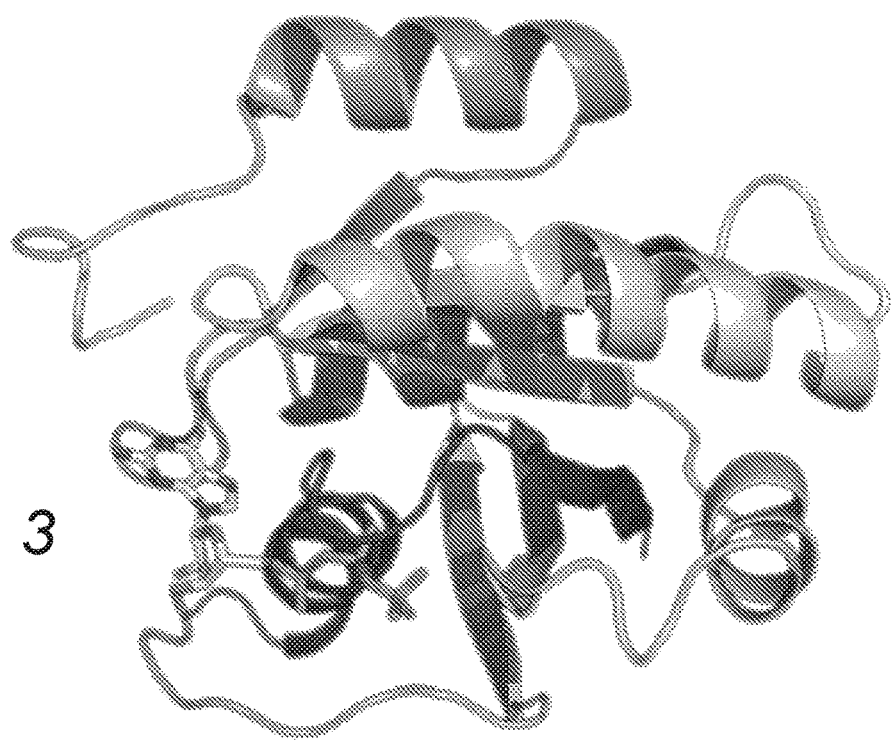
FIG. 3 is a homology ribbon model for Rit1.

In view of these and other observations, the inventors calculated a homology model in which the structure of Rit1 was modeled after a PDB entry with incomplete loops using Ras as a template. The structure of so calculated model is shown as ribbon model in FIG. 3. In this model the area of interest was highly conserved between the Rit1 and Ras proteins, and this calculated model was employed for virtual screening of about 1.1 million different compounds in silico. The best binders among the thusly tested compounds were noted and binding/activity on signaling was verified in vitro as is further described in more detail below.

Figure 4:
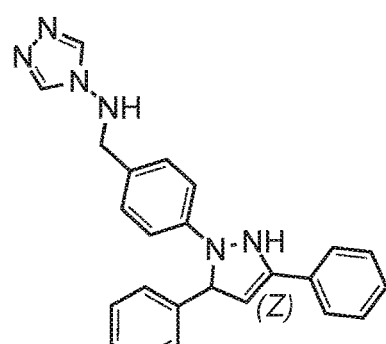
FIG. 4 illustrates one exemplary compound (A1233) that was shown to bind to Rit1.
Figure 4:
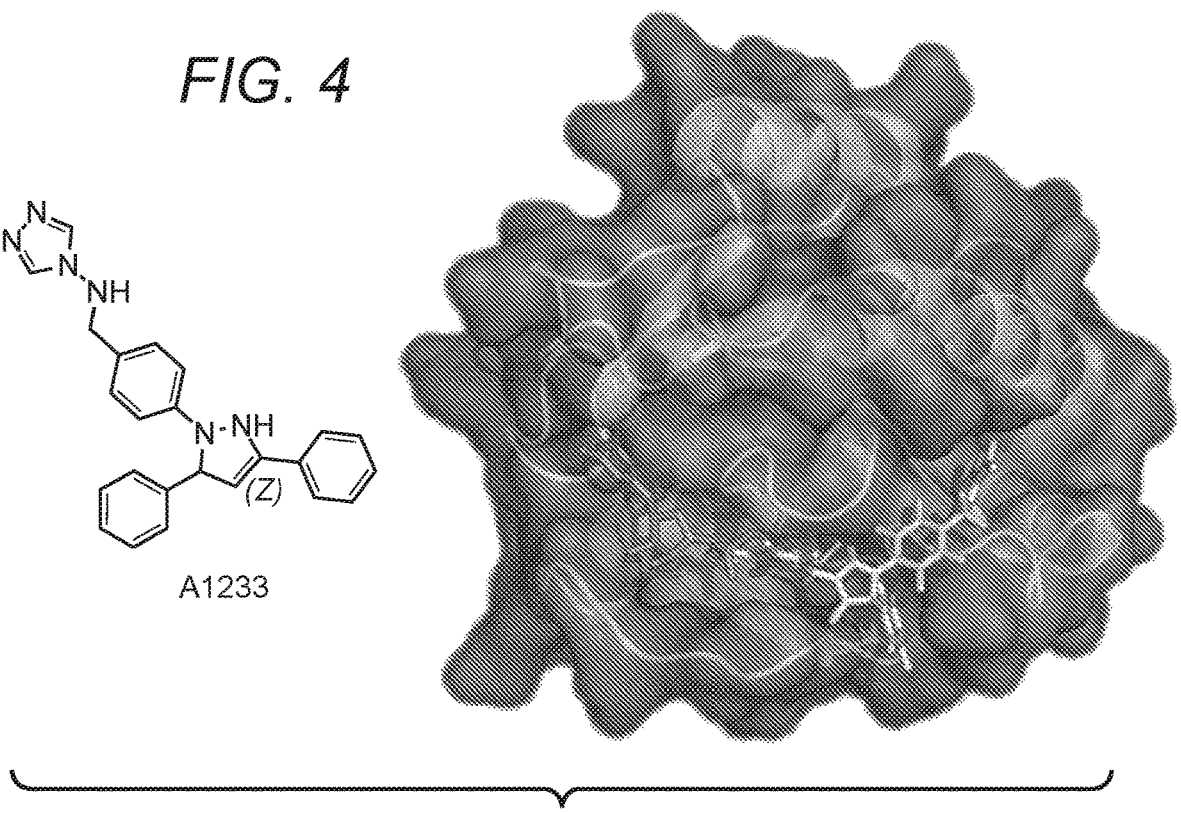
Figure 5:
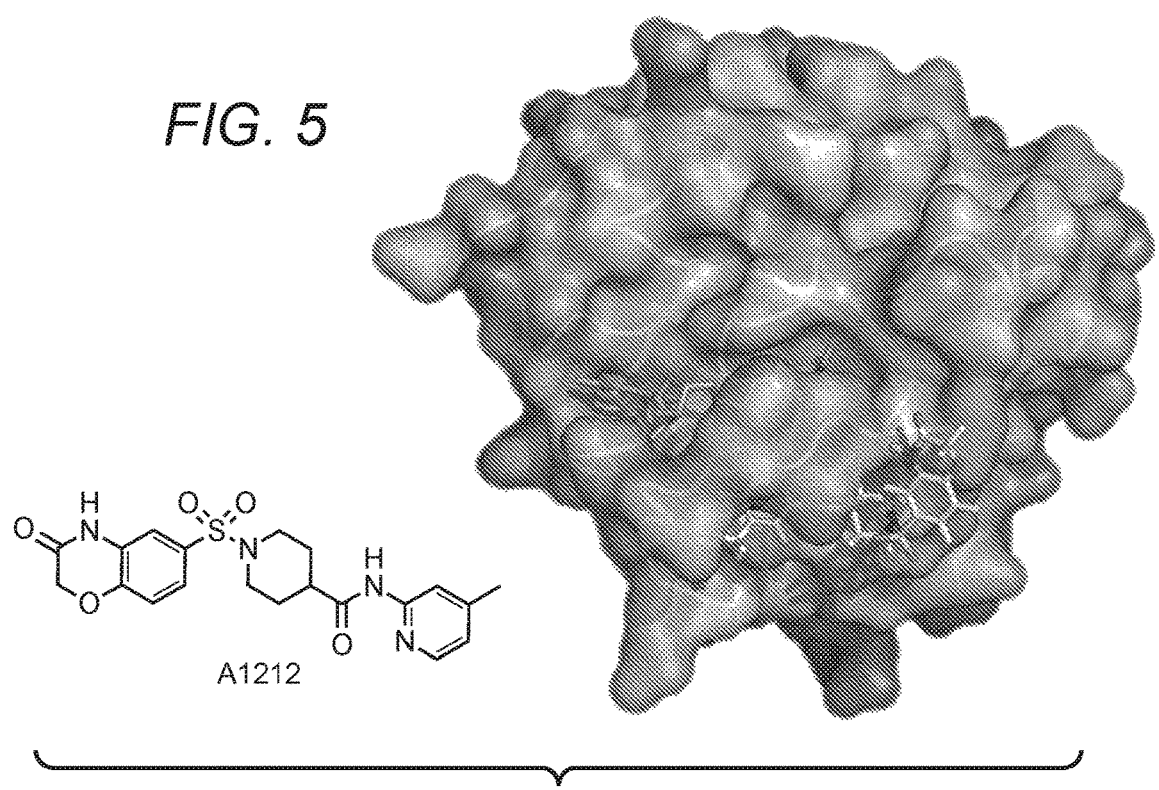
FIG. 5 illustrates another exemplary compound (A1212) that was shown to bind to Rit1.

FIG. 4 illustrates one exemplary compound (A1233) that was calculated to bind to Rit1 with high affinity and to bind in a motif that partially overlapped the GTP binding domain. In another example, as can be seen in FIG. 5, another compound (A1212) was identified that was calculated to bind to Rit1 with high affinity and in a position proximal but not overlapping with the GTP binding domain. Based on screening results and other observations (data not shown), the inventors discovered that various Rit1 inhibitors can be identified and prepared, and that such inhibitors have potent and specific inhibitory action as is also shown in more detail below.

Using the selected screening hits and additional computational analyses, the inventors thus contemplate in one aspect of the inventive subject matter that selected small molecule Rit1 inhibitors will generally have a structure according to Formula I

Formula I wherein G is an optionally substituted 5- or 6-membered ring, W is CH$_2$, S(O), SO$_2$, or null, M is an optionally substituted 6-membered ring, A is a 5-membered ring, and E and D are independently an optionally substituted 5- or 6-membered ring.

While not limiting to the inventive subject matter it is generally preferred that G is an optionally substituted heterocyclic ring, or an optionally substituted aromatic ring. For example, where G is a 5-membered ring aromatic or heterocyclic ring, G may be a pyrrole, a pyrrolidine, a thiophene, a thiolane, a pyrazole, an imidazole, a pyrazolidine, an imidazolidine, a thiazole, an isothiazole, a thiazolidine, an isothiazolidine, a triazole, a thiadiazole, an oxadiazole, or a tetrazole. Alternatively, where G is a 6-membered aromatic or heterocyclic ring, G may also be pyridine, a piperidine, a diazine, a piperazine, an oxazine, a morpholine, a thiazine, a trizine, and a tetrazine. It should also be appreciated that G may be substituted with one or more radicals, and especially contemplated radicals include NH$_2$, NO$_2$, OH, O, S, SH, lower alkyl, and halogen.

With respect to M it is contemplated that M preferably is/comprises an aromatic ring, a heterocyclic ring, or a phenyl, each of which may be substituted with one or more substitutents (e.g., NH$_2$, NO$_2$, OH, O, S, SH, lower alkyl, halogen). For example, M may be an optionally substituted phenyl, piperidine, or cyclohexadiene. Likewise, A may vary considerably, however, it is generally preferred that A is an aromatic ring and especially a pyrazolidine or a pyrazoline. E and F are independently an optionally substituted aromatic 5- or 6-membered ring, which may include a heteroatom or which may be fused to another ring. For example, E and/or D may be an optionally substituted phenyl, pyrrolidine, pyrrole, pyridine, or morpholine. As noted before, preferred substituents for E and D include NH$_2$, NHalkyl, NHacetyl, NO$_2$, OH, O, S, SH, lower alkyl, and halogen, however, other substituents are also deemed suitable.

Suitable optionally substituted aryl or heteroaryl groups for the compounds presented herein include aromatic monocyclic or polycyclic groups, typically comprising between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

Suitable heteroaryl groups will typically include aromatic monocyclic or polycyclic groups comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The term "heterocyclic" or "heterocycloalkyl" herein alone or as part of another group refers to a cycloalkyl group (nonaromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur. Examples of "heterocyclic" or "heterocycloalkyl" groups include piperazine, piperidine, morpholine, thiomorpholine, pyrrolidine, imidazolidine and thiazolide.

The term "optionally substituted" as used herein means that the aryl, heterocyclyl, or other group may be substituted at one or more substitutable positions by one or more groups independently selected from alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

Therefore, the various moieties or functional groups for variables in the formulae may be substituted by one or more suitable substituents. Examples of useful substituents are those found in the exemplary compounds, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

Among other compounds, especially contemplated compounds include those according to Formula Ia

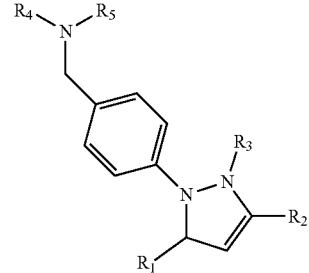

Formula Ia

Figure 8B:
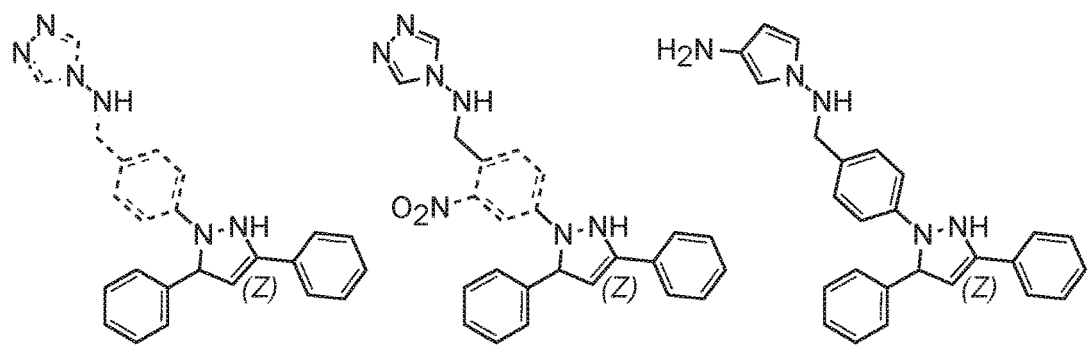
Figure 8B:
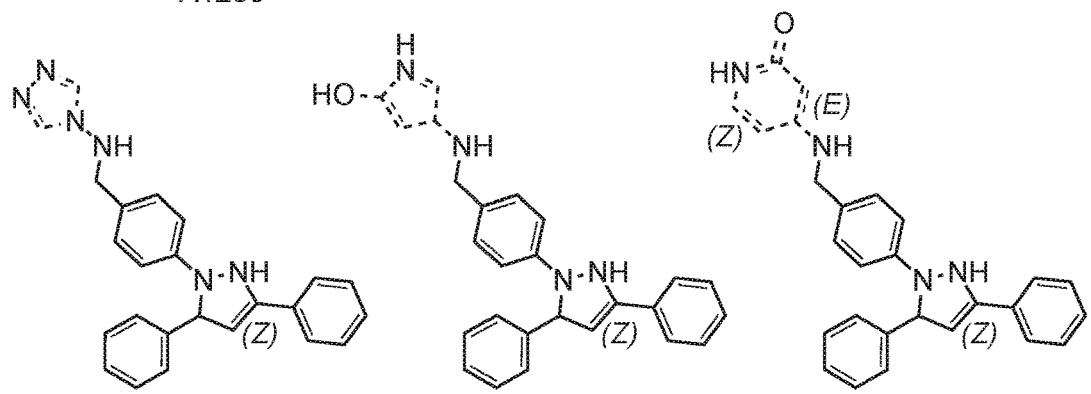
Figure 8B:
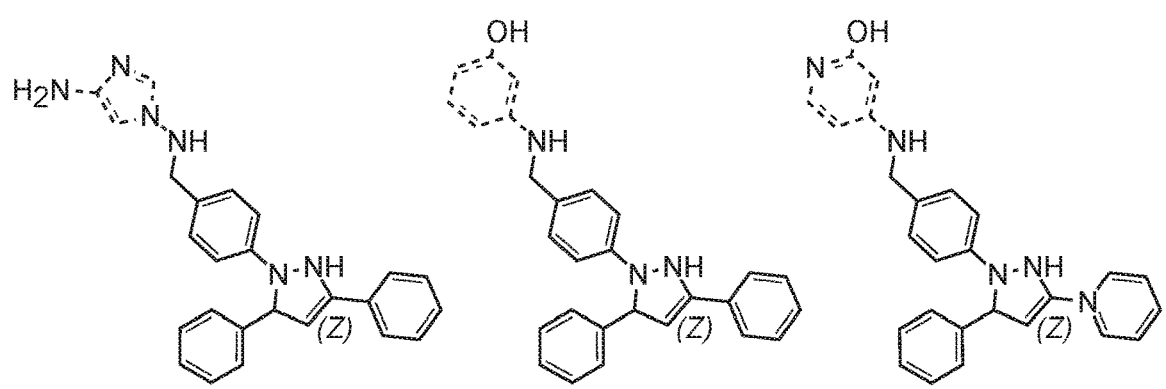
Figure 8B:
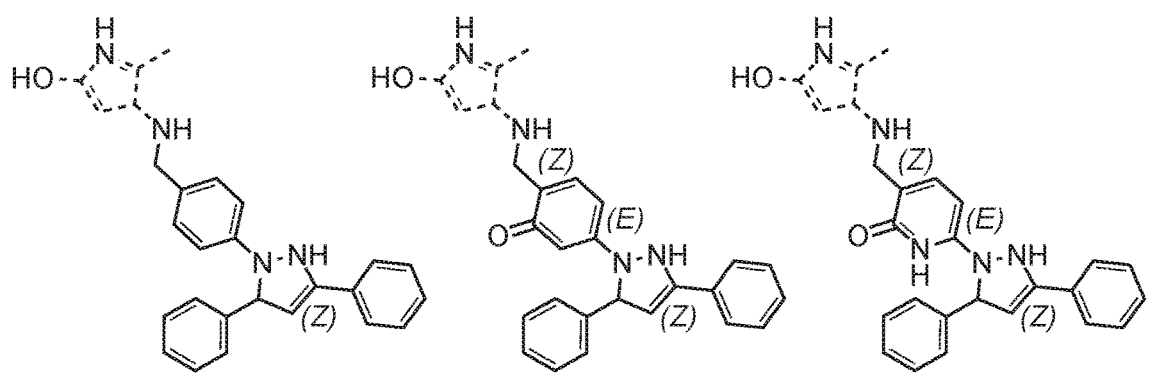

In such compounds, $R_1$, $R_2$, and $R_4$ are independently aryl, heteroaryl, heterocycle, or fused heterocycle, each optionally substituted, and $R_3$ and $R_5$ are independently hydrogen or lower alkyl, or other sterically relatively small substituent. For example, in preferred aspects of the inventive subject matter, $R_3$ and $R_5$ are hydrogen, and/or at least one of $R_1$ and $R_2$ is phenyl. Additionally, it is contemplated that $R_4$ is a 5- or 6-membered heterocyclic ring (e.g., triazole, imidazole, pyridine, etc.). Still further contemplated exemplary compounds suitable for use herein are shown in FIGS. 8A-8B.

In yet another aspect of the inventive subject matter, the inventors also contemplate that suitable small molecule Rit1 inhibitors will generally have a structure according to Formula II

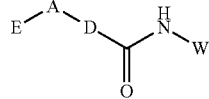

Formula II wherein E is an optionally substituted fused ring system having two rings, A is $CR_1R_2$, S(O), or $SO_2$, wherein $R_1$ and $R_2$ are independently selected form the group consisting of H, halogen, and lower alkyl; and D and W are independently an optionally substituted 6-membered ring.

Most preferably, E comprises a phenyl or a heterocyclic ring, or a phenyl ring fused to a morpholino ring. Of course, it should be recognized that E may be substituted with a radical (e.g., $NH_2$, $NO_2$, OH, O, S, SH, lower alkyl, halogen). It is further generally preferred that A is $SO_2$, $CH_2$, or C (lower alkyl)$_2$, and/or that D is cyclohexane or piperidine. While not limiting to the inventive subject matter, it is contemplated that W is/comprises an aromatic ring (e.g., phenyl or pyridine).

Therefore, contemplated compounds may have a structure according to Formula IIa

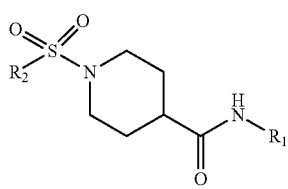

Formula IIa in which $R_1$ and $R_2$ are independently aryl, heteroaryl, heterocycle, or aryl fused to a heterocycle, wherein each of $R_1$ and $R_2$ could be independently optionally substituted. For example, preferred compounds include those where $R_2$ comprises a phenyl, a heterocyclic ring, or a phenyl ring fused to a morpholino ring. $R_1$ in such compounds may comprise a phenyl or a pyridine. Consequently, an exemplary compound may have a structure according to Formula IIb

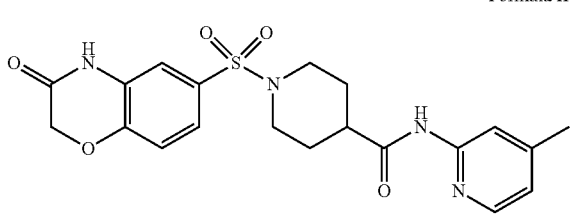

Formula IIb

For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

It will be appreciated by those skilled in the art that compounds of the invention having a chiral center may exist in, and may be isolated in, optically active or racemic forms. It is to be understood that the compounds of the present invention encompasses any racemic, optically-active, regioisomeric or stereoisomeric form, or mixtures thereof, which possess the therapeutically useful properties described herein. Where the compounds of the invention have at least one chiral center, they may exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

It is well known in the art how to prepare optically active forms (e.g., by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

Furthermore it should be noted that the compounds contemplated herein may be prepared as prodrugs. The term "prodrug" as used herein refers to a modification of contemplated compounds, wherein the modified compound exhibits less pharmacological activity (as compared to the modified compound) and wherein the modified compound is converted within a target cell (e.g., cancer cell) or target organ/anatomic structure (e.g., lung) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B.

Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

In yet another aspect of the inventive subject matter, the inventors further contemplate pharmaceutical compositions that are formulations of one or more of compounds presented herein and a pharmaceutically-acceptable carrier. Thus, the inventive subject matter is also directed to a pharmaceutical composition for administration to a mammalian subject, which may include one or more of the compounds presented herein (or pharmaceutically acceptable salts thereof).

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

It is generally contemplated that the compounds according to the inventive subject matter may be employed in various therapeutic or prophylactic compositions to affect any condition and/or disease associated with dysfunction (e.g., deviation of activity of at least 10% and more typically at least 20% relative to normal in healthy person) of Rit1, or where modulation of normal activity is desired for a particular purpose. Thus, and viewed from a different perspective, contemplated compositions may be used for treatment of diseases or conditions where reduction of Rit1 activity is therapeutically or prophylactically desirable. Therefore, particularly contemplated conditions and diseases include those that are sensitive to changes of Rit1 activity. For example, contemplated compounds and compositions may be useful in the prevention and/or treatment of cancer (growth inhibition or reduction of growth of the cancer tissue or cells), and particularly cancer that is associated with dysfunction of Rit1 activity, as well as treatment or prevention or reduction of metastasis of a tumor. For example, conditions and diseases to be treated with contemplated compounds and compositions especially include various cancers, and particularly uterine, bladder, lung, and skin (melanoma) cancers.

Depending on the particular purpose, it should also be recognized that contemplated compounds may be combined (in vivo, or in a pharmaceutical formulation or administration regimen) with at least one other pharmaceutically active agent to additively or synergistically provide a therapeutic pr prophylactic effect. Concentrations of second pharmaceutically active ingredients are typically at or preferably below those recommended for stand-alone administration, however, higher concentrations are also deemed suitable for use herein. Most typically, additional pharmaceutical agents include antineoplastic drugs (e.g., angiogenesis inhibitors, antimetabolites, replication inhibitors, drugs targeting DNA repair, proteasome inhibitors, DNA alkylating agents, etc.), immune therapeutic drugs (e.g., modified NK cells, modified T-cells, viral expression systems for delivery of cancer neoepitopes, checkpoint inhibitors, etc.), analgesic drugs, anti-inflammatory drugs, etc.

Therefore, contemplated pharmaceutical compositions will especially include those in which contemplated compounds (and optionally further pharmaceutically active ingredients) are provided with a suitable carrier, wherein contemplated compounds are preferably present at a concentration effective to modulate Rit1 signaling in an organism and/or target organ to a degree effective to reduce or prevent cancer growth and/or metastasis.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 100 microM, more typically between 1 nM and 50 microM, and most typically between 10 nM and 10 microM. The recitation of ranges should be interpreted as being inclusive of their endpoints and are intended to serve as a shorthand method of referring individually to each separate value falling within the range. Unless otherwise indicated herein, each individual value is incorporated into the specification as if it were individually recited herein.

The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

U.S. Pat. Nos. 5,916,596, 6,506,405 and 6,537,579 teach the preparation of nanoparticles from the biocompatible polymers, such as albumin Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Therefore, contemplated pharmaceutical compositions will especially include those in which contemplated compounds (and additional pharmaceutically active ingredients) are provided with a suitable carrier, wherein contemplated compounds are preferably present at a concentration effective to reduce cell proliferation of a cancerous cell, number of circulating or metastatic cells, or tumor mass to a degree effective to reduce and more preferably to treat signs and symptoms of a disease associated with Rit1 activity. Viewed from a different perspective, contemplated compounds are present in a composition in an amount effective to treat a cancer, and a cancer associated with Rit1 overexpression or over-activity.

The term "therapeutically effective amount" refers to the amount of the compound or pharmaceutical composition that will elicit a biological or medical response of a tissue, system, animal or human that is being sought by the researcher, veterinarian, medical doctor or other clinician, e.g., reduction of tumor growth and/or burden, reduction of occurrence or multiplicity of metastasis, reduction of morbidity and/or mortality.

The terms "administration of a compound" or "administering a compound" refer to the act of providing a compound of the invention or pharmaceutical composition to the subject in need of treatment. Where two or more compounds ad administered, co-administration is typically preferred with the co-administration being either via a combination formulation, or via parallel or subsequent administration of the two compounds. Most typically sequential co-administration will be performed such that the first compound is present in the patient's body in measurable quantities when the second compound is administered.

Experimental Data and Results

The following examples are provided to further illustrate the present invention but, of course, should not be construed as in any way limiting its scope. In general, it should be appreciated that contemplated compounds will include all those that can be identified in an in silico approach using a homology model of Rit1 (e.g., using SWISS-MODEL and Ras sequences for conserved areas) and commercially available molecular docking software (e.g., DOT2.0 (SDSC; Journal of Computational Chemistry, Volume 34, Issue 20, pages 1743-1758, 30 Jul. 2013), AutoDock (Molecular Graphics Laboratory, The Scripps Research Institute, La Jolla) or web services (e.g., SwissDock, using CHARMM force field with EADock DSS), to name a few.

Once desirable candidate compounds are identified in the in silico screening, in vitro inhibition assay can then be used as exemplarily described below. Most preferably, desirable compounds will have an $IC_{50}$ of equal or less than 10 µM, even more preferably of equal or less than 1 µM, and most preferably of equal or less than 100 nM, and will have no apparent toxicity at the $IC_{50}$ as measured above. Such compounds (typically having $IC_{50}$ of equal or less than 10 µM) can then be further modified to ascertain structure activity relationship and to produce compounds with even higher potency, increased bioavailability, and/or reduced toxicity.

Figure 6A:
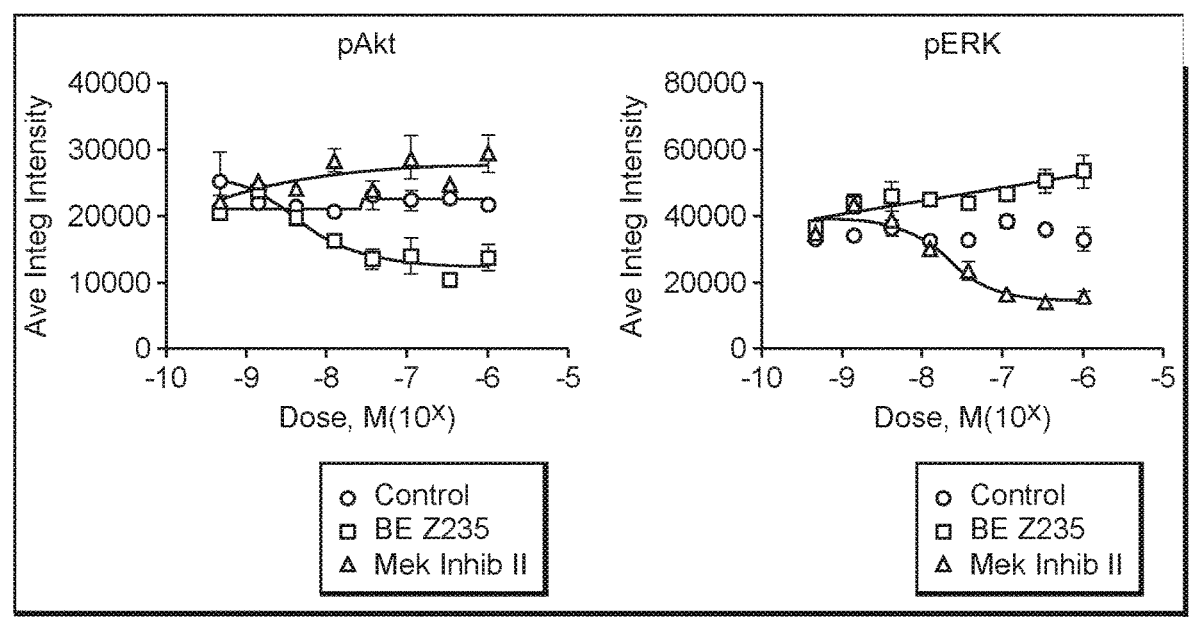

For example, one or more mutant Rit1 cancer cell lines can be tested for their activity in disrupting Rit1 dependent signaling. Analogous experiments with non-Rit1 mutant cancer cell lines may be employed to ascertain specificity against Rit1, while analogous experiments with non-cancer cell lines may be performed for evaluation of toxicity. FIG. 6A illustrates a typical setup where Akt and Erk phosphorylation is measured as a function of inhibitors that were pre-incubated with mutant Rit1 cells. Here, the mutant cells were NCI-H2110 cells, while the inhibitors were MEK Inhibitor II and BEZ235 (imidazoquinoline derivative with PI3K inhibitor activity). The graphs in FIG. 6A depict the effect of the inhibitors on pAKT and pERK as a function of concentration.

Figure 7:
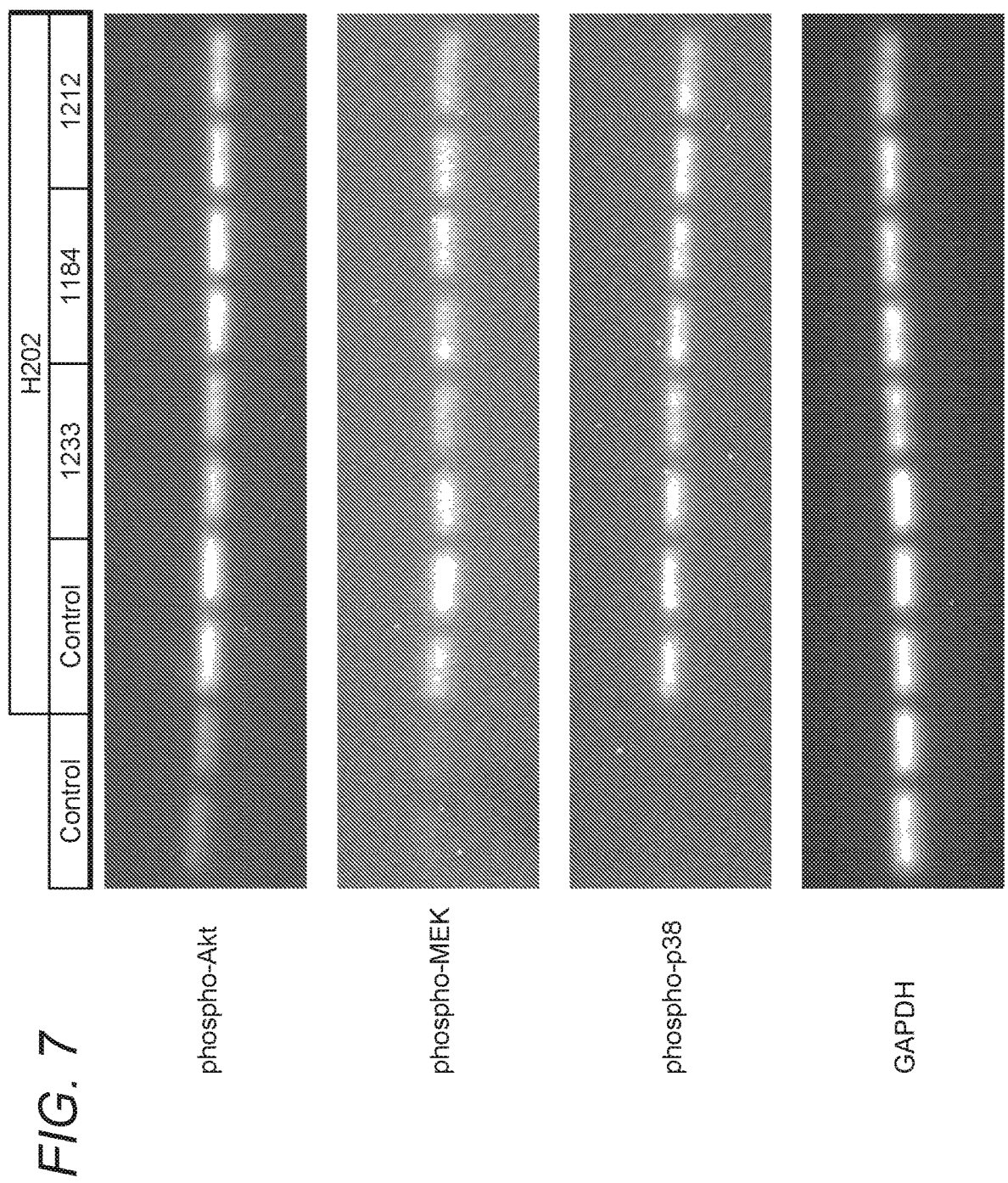
FIG. 7 is a photograph of phosphorylation assays after cell stimulation with $H_2O_2$ in the presence of selected contemplated compounds.

Using a system as described above, the inventors determined for various cell lines and different cancer types selected of contemplated compounds as shown in the Table of FIG. 6B where higher inhibition is illustrated with a higher number of X marks. As can be readily seen from the data, certain of the compounds had specific inhibition of pAkt/pERK in NCI-H2110 (Rit1 mutant) cells. FIG. 7 depicts the results of an experiment in which HeLa cells were subjected to $H_2O_2$ to stimulate apoptotic cell death pathways and in which the effect of contemplated compounds on phosphorylation of Akt MEK and p38 is shown.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise.

What is claimed is:

1. A pharmaceutical composition, comprising a compound having a structure according to Formula Ia and a pharmaceutically acceptable carrier;

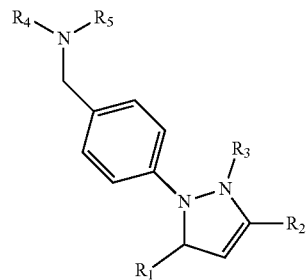

Formula Ia wherein $R_1$, $R_2$, and $R_4$ are independently aryl, heteroaryl, heterocycle, or fused heterocycle, each optionally substituted; and wherein $R_3$ and $R_5$ are independently hydrogen or lower alkyl.

2. The pharmaceutical composition of claim 1 wherein $R_3$ and $R_5$ are hydrogen.

3. The pharmaceutical composition of claim 1 wherein at least one of $R_1$ and $R_2$ is phenyl.

4. The pharmaceutical composition of claim 1 wherein $R_4$ is a 5- or 6-membered heterocyclic ring.

5. The pharmaceutical composition of claim 1 wherein $R_4$ is a triazole, an imidazole, or a pyridine.

* * * * *